US00PP14832P3

(12) United States Plant Patent
van der Voort

(10) Patent No.: US PP14,832 P3
(45) Date of Patent: May 25, 2004

(54) LILY PLANT NAMED 'SOLDERA'

(50) Latin Name: *Lilium l.*
Varietal Denomination: Soldera

(75) Inventor: Cees A. van der Voort, Katwijk (NL)

(73) Assignee: Vletter & Den Haan Beheer B.V. (NL)

( * ) Notice: Subject to any disclaimer, the term of this patent is extended or adjusted under 35 U.S.C. 154(b) by 0 days.

(21) Appl. No.: 09/521,607

(22) Filed: Mar. 9, 2000

(65) Prior Publication Data

US 2002/0059672 P1 May 16, 2002

(51) Int. Cl.[7] ..... A01H 5/00
(52) U.S. Cl. ..... Plt./315
(58) Field of Search ..... Plt./315

(56) References Cited

U.S. PATENT DOCUMENTS

PP8,925 P * 10/1994 Van der Salm ..... Plt./315

OTHER PUBLICATIONS

UPOV ROM GTITM Computer Database, GTI JOUVE Retrieval software, citations for 'Soldera', Aug. 2000.*

* cited by examiner

*Primary Examiner*—Bruce R. Campell
*Assistant Examiner*—W C Haas
(74) *Attorney, Agent, or Firm*—Foley & Lardner

(57) ABSTRACT

A new and distinct cultivar of Lily plant named 'Soldera' characterized by its large erect to vertical flowers, petals with curled edges, red-purple color and vigorous growth.

1 Drawing Sheet

BACKGROUND OF THE INVENTION

The present invention comprises a new and distinct cultivar of lily plant, botanically known as *Lilium l.,* and hereinafter referred to by the cultivar name 'Soldera'.

'Soldera' is a product of a planned breeding program which had the objective of creating new lily cultivars having many large erect flowers and vigorous growth.

'Soldera' was originated from a hybridization made by the inventor in a controlled breeding program in Rijnsburg, the Netherlands in 1986. The male and female parents were unnamed seedlings of *Lilium l.* oriental hybrids. Both parents are proprietary cultivars used in the breeding program.

'Soldera' was discovered and selected as one flowering plant within the progeny of the stated cross by the inventor, Cees A. van der Voort, during the months of May and June 1986 in a controlled environment in Rijnsburg, the Netherlands.

The first act of asexual reproduction of 'Soldera' was accomplished when scales were taken from the initial selection in October 1988 in a controlled environment in Rijnsburg, the Netherlands by, or under the supervision of, Cees A. van der Voort. Horticultural examination of selected units initiated in May, 1988 has demonstrated that the combination of characteristics as herein disclosed for 'Soldera' are firmly fixed and are retained through successive generations of asexual reproduction.

BRIEF DESCRIPTION OF THE INVENTION

The following traits have been repeatedly observed and are determined to be basic characteristics of 'Soldera' which in combination distinguish this lily as a new and distinct cultivar:

1. many large, erect flowers;
2. slim tepals with curled edges;
3. soft pink color with contrasting orange pollen; and
4. vigorous growth habit.

'Soldera' has not been observed under all possible environmental conditions. The phenotype of the new cultivar may vary significantly with variations in environment such as temperature, light intensity, and daylength without any change in genotype. The following observations, measurements, and comparisons describe plants grown in the experimental research station CPRO-DLO, Wageningen, the Netherlands under conditions which approximate those generally used in commercial practice.

Of the many commercial cultivars known to the present inventor, no other cultivars are similar in comparison to 'Soldera'.

BRIEF DESCRIPTION OF THE DRAWING

The accompanying color photographic illustration shows typical plant and flower characteristics of 'Soldera', with colors being as true as possible with illustrations of this type.

DETAILED BOTANICAL DESCRIPTION

In the following description, color references are made to The Royal Horticultural Society (R.H.S) Colour Chart. The color values were determined between 12 pm and 2 pm in June 1997 at the experimental research station CPRO-DLO, Wageningen, the Netherlands.

The age of the described plant is between 100–120 days after planting the bulbs. The instant plant was grown between 12/13° C. to about until 17/18° C. in a greenhouse. The average daylight during cultivation from April to July was 12–18 hours per days. The light levels vary significantly and were not registered by the applicant.

Fertilizers like Fe and Ca are applied depending on the conditions of the soil in which the bulbs are planted. Average watering rate is 2 times 5 min. per day during the cultivation period. The quantity of irrigation strongly depends on the outside temperatures and light levels.

Origin: Selected crossing from a controlled hybridization program.

Parentage:

*Female parent.*—Unnamed seedling.

*Male parent.*—Unnamed seedling.

Classification:

*Botanical.*—A hybrid of the genus *Lilium l.*

*Commercial.*—Oriental Lily cv. 'Soldera'.

Plant:

*Form.*—A single stem carrying numerous, alternately arranged leaves.

*Height.*—Short to medium for the mature plant, approximately 85 cm, depending on cultivation conditions.

*Growth habit.*—Vigorous. The growth of the plant to about 120 cm depends on temperature and other environmental conditions.

*Stem.*—Circular in transverse section; anthocyanin pigmentation weakly present in spots and stripes; between RHS 199C and RHS 201B; internodal length uniform.

Foliage:

*Quantity.*—Approximately 35–45, depending on cultivation conditions.

*Size of leaf.*—Approximately 8½ cm long and 3 cm wide, depending on cultivation conditions.

*Shape of leaf.*—Generally ovate.

*Texture.*—Hardly any pubescence.

*Color.*—Light-green.

*Bulb.*—Size: 16 to 18 cm in circumference. Color: White/pink.

*Leaf apex shape.*—Pointed.

*Leaf base shape.*—Convex.

*Bulb shape.*—Concave.

*Bud diameter.*—2 cm.

*The RHS color values.*—Upper surface of the foliage: RHS 138 A. Lower surface of the foliage: RHS 138B.

*Bulb color.*—RHS 85D.

Bud:

*Form.*—Tapering like a lancet.

*Size.*—Long, 10 cm in length, depending on cultivation conditions.

*Opening.*—Unfolds normally in standard cultivation conditions.

*Color.*—Red-purple, RHS 60D just before opening.

*Tepals.*—Folded, three visible.

Flower:

*Blooming habit.*—Raceme.

*Size.*—Medium, approximately 16 cm, depending on cultivation conditions.

*Borne.*—Erect to vertical along a longitudinal axis.

*Shape.*—Generally, hexagonal star in form and bowl-shaped in cross-section.

*Tepalage.*—Number of Tepals: 6. Arrangement: Three inner and three outer. Color: Upper Surface: Red-purple, RHS 60D, turning bluish as it ages. Lower Surface: Red-purple, RHS 60D, turning bluish as it ages. Dark purple streaks ranging from RHS 60C to RHC 60B.

*Pedicel.*—Length: Medium, depending on cultivation conditions. Form: Tapering like a lancet.

*Texture.*—Papillose.

*Disease resistance.*—Medium.

*Fragrance.*—Present.

*Lasting quality.*—Excellent.

*Tepal length.*—7–8 cm.

*Tepal width.*—3.5 cm.

*Tepal (inner and outer) shape.*—Pointed.

*Pedicel length.*—2 cm (depending on growing conditions).

*Pedicel diameter.*—1.5 mm.

Reproductive organs:

*Stamens and anthers.*—Arrangements: Anthers form a generally circular pattern at their upper ends. Number: 6. Length: Filament, medium, depending on cultivation conditions. Filaments color: Yellowish-green.

*Pollen color.*—Light-brown.

*Anther color.*—Purplish-red.

*Pistils.*—White/yellow.

*Stigma.*—Dark-purple.

*Ovaries.*—Triangular in shape.

*Plant spread at maturity.*—25–35 cm, depending on growing conditions.

*Disease/pest resistance/susceptibility.*—The instant plant is not resistant against diseases/pests and moderately susceptible compared to the species as a whole.

*Fragrance.*—The instant plant's fragrance is medium strong.

*Lastingness of individual bloom.*—10 days (depending on environmental conditions).

*Cold hardiness.*—Average, can be grown in temperatures from 10–30° C.

I claim:

1. A new and distinct cultivar of Lily plant named 'Soldera', as illustrated and described herein.

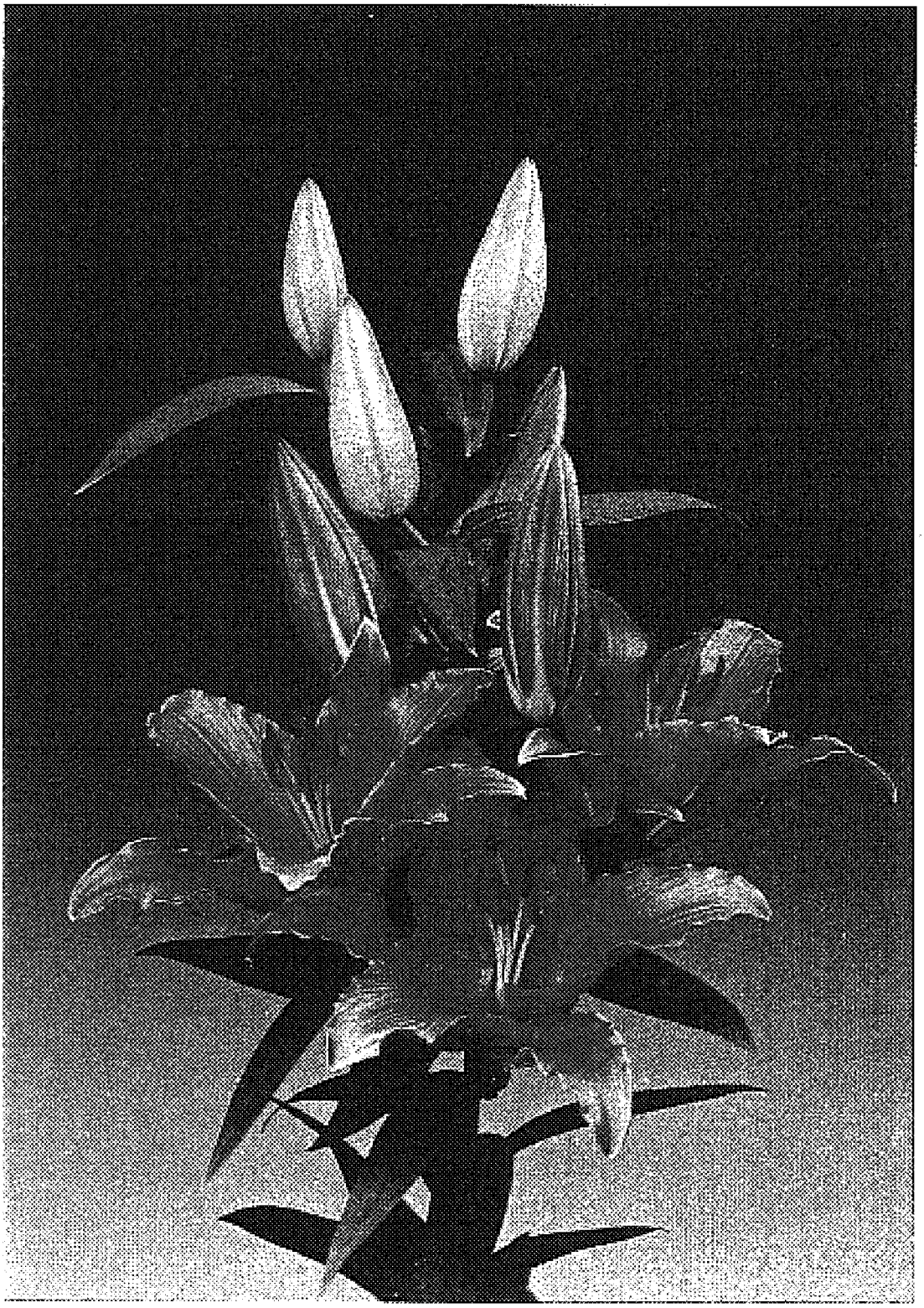

* * * * *